United States Patent [19]

de Mesantourne et al.

[11] Patent Number: 5,171,884

[45] Date of Patent: Dec. 15, 1992

[54] PREPARATION PROCESS FOR GLYOXYLIC ACID BY CATALYTIC OXIDATION OF GLYOXAL IN AN AQUEOUS MEDIUM IN THE PRESENCE OF CATALYTIC QUANTITIES OF PLATINUM

[75] Inventors: Régine de Mesantourne, Cerizay; Pierre Gallezot, Lyons, France

[73] Assignee: Societe Francaise Hoechst, Puteaux, France

[21] Appl. No.: 644,043

[22] Filed: Jan. 22, 1991

[30] Foreign Application Priority Data

Jan. 23, 1990 [FR] France .................. 90 00734

[51] Int. Cl.$^5$ .................. C07C 59/00; C07C 51/00
[52] U.S. Cl. .................. 562/531
[58] Field of Search .................. 562/531, 523

[56] References Cited

U.S. PATENT DOCUMENTS

2,353,159  7/1944  Hull .................. 562/531
2,472,168  6/1949  Mehltretter et al. .................. 562/531

FOREIGN PATENT DOCUMENTS

3918458  12/1989  Fed. Rep. of Germany .
6938197   9/1971  France .
1173264  12/1969  United Kingdom .................. 562/531

Primary Examiner—Arthur C. Prescott
Assistant Examiner—V. Gardner
Attorney, Agent, or Firm—Browdy and Neimark

[57] ABSTRACT

Preparation process for glyoxylic acid in which glyoxal is subjected to a heterogeneous catalytic oxidation in an aqueous medium by oxygen in the presence of catalytic quantities of platinum.

16 Claims, No Drawings

PREPARATION PROCESS FOR GLYOXYLIC ACID BY CATALYTIC OXIDATION OF GLYOXAL IN AN AQUEOUS MEDIUM IN THE PRESENCE OF CATALYTIC QUANTITIES OF PLATINUM

The present invention relates to a preparation process for glyoxylic acid by catalytic oxidation of glyoxal in an aqueous medium in the presence of catalytic quantities of platinum.

Glyoxylic acid, which is an important raw material in organic synthesis, notably for obtaining vanillin, is currently obtained by nitric oxidation of glyoxal. This oxidation can also be carried out by electrochemical means in the anodic section of an electrolytic cell.

However, these processes use indirect oxidation reagents necessitating subsequent purifications which do not lend themselves to continuous operation, and because of this fact their profitability is not satisfactory. Also, obtaining glyoxylic acid by catalytic oxidation of ethylene or of acetaldehyde is known, but the selectivity of such oxidations is poor.

A direct catalytic oxidation of glyoxal into glyoxylic acid by molecular oxygen has never been described. There has now been found, and this constitutes the subject of the present invention, a preparation process for glyoxylic acid, characterized in that glyoxal is subjected to a heterogeneous catalytic oxidation, in an aqueous medium, by oxygen in the presence of catalytic quantities of platinum.

In the advantageous conditions for implementing the invention, the process described above is carried out at a temperature between 20° and 100° C. The reaction will be taken preferably to a pressure between ambient pressure and 20 bars. The glyoxal/platinum molar ratio will be advantageously between 50 and 2000.

When the process of the invention is implemented at atmospheric pressure, it is advantageous to operate with a slight bubbling through of air or better still of pure oxygen. In other cases, the operation is done in a closed vessel in an air or oxygen atmosphere.

Advantageously, platinum is deposited on an inert solid support which is insoluble in water, preferably solid, chosen notably from the group constituted by graphites, carbon blacks and activated charcoals. The platinum will be preferably deposited in the form of fine metallic particles, evenly sized between 1.5 and 2 nm. The inert support chosen could be advantageously an activated charcoal with a large specific surface area, greater than 1000 $m^2$ per gram. By activated charcoal is usually meant a very porous substance obtained by gasification with water vapour or with carbon dioxide of carbon substances incapable of undergoing graphitization.

The metallic platinum could be deposited on the support chosen according to standard techniques or by impregnation with an aqueous solution of hexachloroplatinic acid followed by a reduction, as described by J. M. Dirkx et al., J. Catalysis, 1981, 67, 1-13, or by cation exchange with an aqueous solution of tetramine platinum chloride and reduction according to D. Richard et al, Preparation of Catalyst, Vol. IV, pages 71-81, Elsevier, Amsterdam, 1987. Advantageously, between 2 and 6% by weight of platinum will be deposited on the support. Examination by transmission electron microscope by transmission of these supports enables it to be stated that the average size of the platinum metal particles is approximately 1.5 to 2 nm.

As the oxidation of the glyoxal into glyoxylic acid proceeds, the pH of the reaction medium decreases due to the strong acidity of the glyoxylic acid formed. Thus a convenient means of monitoring the development of the reaction is available. The operation can be carried out, if desired, at constant pH by continuously introducing into the reaction medium a hydrosoluble alkaline agent such as an alkali metal hydroxide like sodium hydroxide or potassium hydroxide in order to salify the glyoxylic acid formed.

The following examples illustrate the present invention without however limiting it.

EXAMPLE 1

Preparation of the catalyst

Activated charcoal of a specific surface area of 1450 $m^2/g$ is agitated for 24 hours at 50° C., in 10 volumes of 2N hydrochloric acid. The suspension is then filtered and the precipitate collected is washed with water until the chloride ions are completely eliminated. This precipitate is then subjected to a partial combustion for 3 hours at 500° C. under an air current of 120 ml/min. After cooling down to ambient temperature, a charcoal is obtained having a specific surface area of 1800 $m^2/g$.

1 g (1.93 mmole) of hexachloroplatinic acid crystallized with 6 molecules of water is dissolved in 20 g of distilled water, then this solution is introduced under an inert atmosphere into an agitated suspension of 7.2 g of charcoal obtained previously and the suspension obtained is agitated at ambient temperature for 330 minutes under an inert atmosphere. The suspension is then cooled down to 0° C. and at this temperature 19.5 g of an aqueous solution of 37% formaldehyde, this being 0.24 moles of formaldehyde, is introduced, then 10 minutes later, 11.6 g of an aqueous solution of potassium hydroxide at 30% by weight, this being 0.21 moles of potassium hydroxide, is introduced. The suspension obtained is then agitated for 16 hours at ambient temperature and filtered. The precipitate is washed with water until the wash waters are neutral and it is then dried under reduced pressure at 100° C. for 13 hours. In this way a catalyst containing 4.2% by weight of platinum metal is obtained in the form of fine metallic particles, evenly sized from 1.5 to 2 nm.

EXAMPLE 2

The following suspension constituted by:
- 304.36 g of an aqueous solution of glyoxal at 0.573% by weight, this being 1.745 g (30 mmoles) of glyoxal,
- 0.750 g of the catalyst prepared in Example 1 containing 4.2% by weight of platinum, this being 31.5 mg (0.161 mmoles) of platinum metal, is agitated at a speed of 400 revolutions per minute, for 110 minutes at 38°±2° C., with a bubbling through of air at 100 ml per minute, maintaining the pH of the reaction medium at 7.7 by the continuous addition of a diluted aqueous solution of potassium hydroxide.

In this way a suspension is obtained containing:
- 2.47 g (22 mmoles) of potassium glyoxylate,
- 0.75 g (4.5 mmoles) of potassium oxalate,
- 0.13 g (2.25 mmoles) of non-converted glyoxal.

The oxidation yield is 73% of the theoretical amount relative to the glyoxal used and the selectivity is 79.3%.

We claim:

1. Preparation process for glyoxylic acid, characterized in that glyoxal is subjected to a heterogeneous catalytic oxidation in an aqueous medium by oxygen in the presence of catalytic quantities of platinum.

2. Process according to claim 1, characterized in that it is carried out at a temperature between 20° and 100° C.

3. Process according to claim 1, characterized in that it is carried out at a pressure between ambient pressure and 20 bars.

4. Process according to claim 1, characterized in that the molar ratio of glyoxal to platinum is between 50 and 2000.

5. Process according to claim 1, characterized in that the platinum is deposited on an inert solid support, insoluble in water.

6. Process according to claim 5, characterized in that the inert support is an activated charcoal of a specific surface area greater than 1000 m$^2$/g.

7. Process according to claim 2, carried out at a pressure between ambient pressure and 20 bars.

8. Process according to claim 2, wherein the molar ratio of glyoxal to platinum is between 50 and 2000.

9. Process according to claim 3, wherein the molar ratio of glyoxal to platinum is between 50 and 2,000.

10. Process according to claim 7, wherein the molar ratio of glyoxal to platinum is between 50 and 2,000.

11. Process according to claim 2, wherein the platinum is deposited on an inert, solid support, insoluble in water.

12. Process according to claim 8, wherein the platinum is deposited on an inert, solid support, insoluble in water.

13. Process according to claim 9, wherein the platinum is deposited on an inert, solid support, insoluble in water.

14. Process according to claim 10, wherein the platinum is deposited on an inert, solid support, insoluble in water.

15. Process according to claim 1, wherein said platinum is in the form of fine metallic particles of size between 1.5 and 2 nm.

16. Process according to claim 1, comprising adding a hydrosoluble alkaline agent to said aqueous medium as the oxidation proceeds to salify the glyoxylic acid formed.

* * * * *